(12) United States Patent
Hassingboe et al.

(10) Patent No.: US 9,155,662 B2
(45) Date of Patent: *Oct. 13, 2015

(54) MULTI-COMPONENT NON-WOVEN

(71) Applicant: Coloplast A/S, Humlebaek (DK)

(72) Inventors: Jens Hassingboe, Graested (DK); Jacob Vange, Helsingoer (DK); Hanne Everland, Bagsvaerd (DK); Rong Weimin, Bagsvaerd (DK)

(73) Assignee: Coloplast A/S, Humlebaek (DK)

( * ) Notice: Subject to any disclaimer, the term of this patent is extended or adjusted under 35 U.S.C. 154(b) by 92 days.

This patent is subject to a terminal disclaimer.

(21) Appl. No.: 13/783,223

(22) Filed: Mar. 1, 2013

(65) Prior Publication Data

US 2013/0175729 A1 Jul. 11, 2013

Related U.S. Application Data

(62) Division of application No. 12/450,954, filed as application No. PCT/DK2008/050090 on Apr. 17, 2008, now abandoned.

(30) Foreign Application Priority Data

Apr. 20, 2007 (DK) ................................ 2007 00585

(51) Int. Cl.
*A61L 15/00* (2006.01)
*A61F 13/00* (2006.01)
*A61L 15/32* (2006.01)

(52) U.S. Cl.
CPC ........... *A61F 13/00987* (2013.01); *A61L 15/32* (2013.01)

(58) Field of Classification Search
None
See application file for complete search history.

(56) References Cited

U.S. PATENT DOCUMENTS

| 4,453,939 | A | 6/1984 | Zimmerman et al. |
|---|---|---|---|
| 6,056,970 | A | 5/2000 | Greenawalt et al. |
| 6,716,526 | B2 | 4/2004 | Weston et al. |
| 7,615,373 | B2 | 11/2009 | Simpson et al. |
| 8,053,559 | B2 | 11/2011 | Nielsen et al. |
| 8,222,166 | B2 | 7/2012 | Chu et al. |
| 2002/0187194 | A1 | 12/2002 | Stimmeder |
| 2004/0110439 | A1 | 6/2004 | Chaikof et al. |
| 2005/0073075 | A1* | 4/2005 | Chu et al. ...................... 264/465 |

FOREIGN PATENT DOCUMENTS

| EP | 0059265 | 9/1982 |
|---|---|---|
| EP | 1 588 722 | 10/2005 |
| GB | 1144552 | 3/1969 |
| WO | WO 94/04282 | 3/1994 |
| WO | WO 99/56798 | 11/1999 |

OTHER PUBLICATIONS

Li et al., Gelatin and gelatin-hyaluronic acid nanofibrous membranes produced by electrospinning of their aqueous solutions, 2006, Biomacromolecules 7(7): 2243-2247.*

* cited by examiner

*Primary Examiner* — Robert Yamasaki
(74) *Attorney, Agent, or Firm* — Coloplast Corp., Coloplast A/S; Nick Baumann (57) ABSTRACT

The formation of a non-woven, free from organic solvent, formed through parallel formation of fibers on a collection device is disclosed. As the individual fibers are dry prior to contact with other fibers, the different contents of the various fiber types do not interact. However, when wetted, the fibers will start to be dissolved, or swell, and the different contents will be released and then interact. For the example of thrombin and fibrinogen, the interaction will initiate the formation of a fibrin coagulum by the cleavage of fibrinogen through the action of thrombin to form fibrin monomers that spontaneously polymerize to form a three dimensional network of fibrin.

3 Claims, 7 Drawing Sheets

Cross section of multi components

Fig 8

MULTI-COMPONENT NON-WOVEN

This is a division of U.S. patent application Ser. No. 12/450,954, filed May 17, 2010, which is a national stage of PCT/DK08/050,090 filed Apr. 17, 2008 and published in English, which has a priority of Danish Application PA 2007 00585, filed Apr. 20, 2007, each of which is hereby incorporated by reference.

BACKGROUND

In many instances it is desired to provide a product with two different, but mixed components. One example is for control of heamostasis. Here it is desired to provide a product with both thrombin and fibrinogen to be released in in situ. However, care has to be taken to ensure the active components do not interact prior to placement in situ.

For this type of products any residual organic solvents in the product can be harmful to the wound site, and should be avoided.

WO99/56798 discloses a product of polysaccharides as polyanionic polysaccharides, alginic acid, chitin, chitosan, and dextran; synthetic materials as polyglycolide, polylactide, polycaprolactone, and fibrin. The product is produced by admixing of the components under high shear conditions to evenly disperse the materials in an organic solvent.

SUMMARY

The present invention discloses the formation of a non-woven, free from organic solvent, formed through parallel formation of fibers on a collection device.

DETAILED DISCLOSURE

One aspect of the present invention relates to a multi component non-woven of fibers of a natural protein structure, comprising at least two fiber types of different compositions.

One aspect of the invention relates to a multi component non-woven as described wherein at least one of the fiber types comprises thrombin and at least one other fiber type comprises fibrinogen.

In one embodiment of the invention, one of the fibre types comprises an analgesic. For a wound care device for treatment of pain, this is particularly advantageous. The analgesic incorporated into the fibers of the present invention is released over time locally to the wound. Preferably, the release of the analgesic is so low that no systemic effect is seen. Thus, the concentration of analgesic in the device of the invention may be so low that little or no effective systemic plasma concentration can be found. This will reduce or even eliminate the possible systemic side effects of the analgesic, and at the same time provide the patient with maximum safety, as oral doses or topical doses on intact skin can be taken at the same time. Thus, the device renders it possible to ingest additional medication, if needed, orally or topically of the same type as in the wound care device, without the risk of overdosing. Furthermore, side effects are lowered and compliance will be better as well as the HQoL.

For different analgesics, the plasma concentration for systemic effect in the lowest range is reported to be as follows given as examples: Acetylsalicylic acid: 270 μg/ml; Ketoprofen: 3 μg/ml; Ibuprofen: 10 μg/ml; Piroxicam: 1 μg/ml. Thus, a wound care device for treatment of pain in a wound releasing analgesics locally to a wound site may be designed in such a way that the plasma concentration is under the lowest range for systemic effect in the body.

This is also true for other anti-inflammatory pain reliving compositions being suitable for incorporation into the multi component non-woven (the device) of the invention.

Prostaglandins, leukotrienes, and thromboxanes are key inflammatory mediators produced from arachidonic acid. Inhibition of the synthesis of these mediators is the target of the most highly prevalent class of anti-inflammatory drugs, the NSAIDs. Inflammatory mediators will stimulate pain nociceptors and as a result pain is produced.

Inflammatory pain is believed to be important for the actually feeling of chronic or persistent wound pain. It is believed that tissue injury as e.g. seen in chronic wounds triggers the release of multiple inflammatory mediators that themselves, alter nociceptor function. The level of inflammation is therefore elevated and may be lowered by addition of anti-inflammatory drugs locally to the wound that would lead to pain relief. Preferably the pain relieving composition comprises an anti-inflammatory painkilling agent that blocks the production of inflammatory mediators produced from arachidonic acid.

NSAIDs (non-steroid anti-inflammatory drugs) generally have analgesics and antipyretic properties along with their anti-inflammatory capabilities. Anti-inflammatory pain killing agents interact with enzyme targets such as cyclooxygenase-inhibiting NSAIDs. The enzymes PGHS (prostaglandin H synthease), commonly know as COX (cyclooxygenase), is responsible for processing arachidonic acid into inflammatory mediators. COX comes from two isoforms COX 1 and COX 2. COX 1 is produced in a more or less constant level at all times and is involved in forming the prostaglandins that perform several important functions, including protection of the gastric mucosa and support of renal function. Consequently, inhibitors of COX 1 may interfere with the gastric mucosa and renal function. COX 2, which is inducible, is expressed after tissue injury and promotes inflammation. Thus, selective inhibition of COX-2, with sparing of COX 1 activity, should be expected to block inflammation without gastric and renal side effects upon oral administration. However, use of COX 1 locally in an open wound setting will not produce any systemic side effects. Classical NSAIDs acts on both COX 1 and COX 2 whereas newer drugs work selectively on COX 2.

Thus, in one embodiment of the invention the analgesic may be capable of inhibiting mediators responsible for processing arachidonic acid into inflammatory mediators.

In preferred embodiment of the invention the analgesic may be capable of inhibiting COX 1 and COX 2.

In one embodiment of the invention the analgesic may be capable of specifically inhibiting COX 2. The analgesic may comprise one or more compounds chosen from the group of anti-inflammatory compositions such as Phenylpropionic acids, Phenelacetic acids, Indoleacetic acids, Pyrroleacetic acids, N-Phenylacetic acids, Salicylates, Enolic acids, Phenols, Non-acids or Coxibs.

Examples of such compounds for the analgesic may be: Propionic acid derivatives such as Naproxen, Ibuprofen, Ketoprofen, Fenoprofen, Flurbiprofen Dexibuprofen or Tiaprofenic acid, Acetic acid derivatives such as Diclofenac, Alclofenac, Fenclofenac, Etodolac, Aceclofenac, Sulindac or Indomethacin, Pyrroleacetic acids such as Ketorolac or Tolmetin, N-Phenylacetic acids such as Mefenamic acid, Salicylates such as Acetyl salicylic acid (Aspirin), Salicylic acid or Diffunisal, Pyrazolon derivatives such as Phenylbutazone, Oxicam derivatives such as Piroxicam, Tenooxicam, Meloxicam or Lornoxicam, Enolic acid derivatives Aminopyrene or antipyrene, Phenols such as Acetaminophen or Phenacetin, Non-acid derivatives Nabumeton, Coxib derivatives such as Celecoxib or Rofecoxib.

Compounds inhibiting COX 2 specifically may be Coxib derivatives such as Celecoxib or Rofecoxib.

In one embodiment of the invention the analgesic is Ibuprofen.

In another embodiment of the invention the analgesic is Ketoprofen.

Thus, a particular embodiment of the invention relates to a non-woven wound dressing with fibers comprising an analgesic. A particular useful construction comprises a first wound-contacting layer of fibers with an analgesic, and a second layer of fibers without the analgesic. The first layer may have a lower cross-binding and/or smaller diameter (and thereby a higher release) than the fibers of the second layer.

The solution provided herein is a solid product, a non-woven, which is easier to handle and administer as opposed to double-syringe applicators known in the art. As the individual fibers are dry prior to contact with other fibers, the different contents of the various fiber types do not interact. However, when wetted, the fibers will start to be dissolved, or swell, and the different contents will be released and then interact. For the example of thrombin and fibrinogen, the interaction will initiate the formation of a fibrin coagulum by the cleavage of fibrinogen through the action of thrombin to form fibrin monomers that spontaneously polymerize to form a three dimensional network of fibrin.

The contents of the fibers will be released as the fibers get dissolved. Hereby is a controlled release obtained.

Materials applicable to present invention are natural protein structures, alone or in combinations, particular preferred are those originating from the ECM. Examples of such materials are collagen, keratin, fibrin, elastin, laminin, vimentin, vitronectin, reticulin, fibrinogen and derivatives of these and the like found in a native or denaturated form. In one embodiment the natural protein is not fibrin.

As illustrated in the examples, the invention is particularly well suited for gelatin, why it is particularly preferred that the natural protein structure is gelatin. Gelatin is an example of a poor fiber forming material, which by the described process in this patent can be made into a fibrous non-woven material. The gelatin fiber is still wet and sticky when it leaves the nozzle. The fiber formation is therefore enhanced if the collection of a fiber is not in a small area, but spread over the collection device. This can be obtained if the fiber ejected from the nozzle hits the collecting device at an angle as described in example 4 where the fibers are sprayed on the inside of an almost vertical rotating cylinder that is close to parallel to the nozzle, or if the collecting device is perpendicular to the nozzle, it has to move at a sufficient speed to spread the fibers. Too slow a speed will result in the fibers sticking together while still wet and forming a more film-like structure.

A particular advantage to Gelatin is the diversity of products possible, with different degrees of x-binding. A non-woven with very little cross-binding will be almost dissolvable, whereas a heavily cross-bound non-woven will stay in the body for a month or two, making sustained release for a long time at a particular site possible. This is particularly useful in the present invention by adding various degrees of polycarboxylic acid to the spinning solution for each fiber type. Hereby a burst release (low cross-binding, small amounts of polycarboxylic acid) can be obtained along with a sustained release (higher cross-binding, higher amounts of polycarboxylic acid).

In one aspect of the invention the fibers are biodegradable fibers. This means a fiber that disappears; is hydrolysed, is broken down, is biodegraded/bioresorbable/bioabsorbable, is dissolved or in other ways vanish from the wound site when in contact with wound exudates, blood or other body fluids. This is a huge clinical advantage as there is nothing to remove from the wound. It is typically preferred that the scaffold is broken down during 1 day to 10 weeks—depending on the application. For open wound applications, it is preferred that the scaffold is broken down during 1-10 days, such as 2-7 days.

One way of manufacturing the present non-woven is by producing fibers of a natural protein structure comprising the steps of:
(a) ejecting an aqueous solution of the natural protein structure through a nozzle, wherein the aqueous solution comprising <25% low molecular weight alcohol; while
(b) emitting pressurized air from air jet bores to attenuate or stretch the natural protein structure fiber; while
(c) collecting the fibers on a collecting device.

This method allows very thin fibers to be extruded by a method that can be run in commercial scale. The method according to the invention is equally applicable to protein structures that are poor fiber makers as well as naturally fiber forming proteins. Gelatin has low cohesive strength and has been hard to manufacture fibers of. The present technique has proven applicable to make gelatin fibers even from water without the use of organic co-solvents.

The multi component non-woven is produced by setting up two systems and, at the same time, ejecting the fibers to the collection device. Hereby is obtained that the fibers are formed, optionally gelled, and dried prior to being in contact with each other.

Non-woven fibrous structures are produced by extruding a material through a nozzle, which due to its structure allows air from nozzles adjacent to the extruding nozzle to enhance the fiber formation by drawing and swirling the material.

The pressurized air is emitted from air jet bores. This attenuates or stretches the natural protein structure fiber by letting pressurized air be ejected from the air jet directed downwardly and substantially tangential to the nozzle (WO94/04282). The air also dries the fibers. Preferably, the pressurized air is blown from a source as close to the orifice as possible, creating a substantially tangentially, downwardly oriented pressurized air flow.

The process and the apparatus is disclosed in detail in WO94/04282.

When the aqueous solution is ejected from the nozzle a thin fiber is formed. Given the high surface area to volume ratio of these fibers, solvent evaporation occurs relatively quickly even when operating with aqueous solutions at ambient temperature and atmospheric pressure. It is appropriate to adjust temperature of both ejected polymer and air such that the formed fibers are dry enough to maintain the formed structure, but not dried too fast. When fibers are not too rapidly dried the gelatin molecules will have time to orient on a molecular level. This is related to the inherent gel-sol properties of gelatin. When subsequent treating the fibers with heat the fibers will cross-link more effectively if the gelatin has been allowed to gel.

The present method avoids the need for biologically toxic solvent systems. Thus, the present process allows real-time fabrication of hybrid protein-cell constructs, and constructs of biologically active constituents: discrete ECM regions, enzymes, analgesics or the like.

In one aspect of the invention particles are suspended in the aqueous solution prior to ejection. As the diameter of the nozzle is wider than the diameter of the formed fibers, the particles can have any diameter, up to the diameter of the nozzle, or the particles can be smaller than the diameter of the fibers. Wet, soft, and pliable particles of even larger diameter than the nozzle may be ejected. Thus, in one aspect of the invention the particles suspended in the aqueous solution have a mean diameter wider than the mean diameter of the fibers.

It is preferred that the particles are ExtraCellular Matrix (ECM) particles. ECM is the non-cellular portion of animal or human tissues. The ECM is hence the complex material that surrounds cells. In broad terms there are three major components in ECMs: fibrous elements (particularly collagen, elastin, or reticulin), link proteins (e.g. fibronectin, laminin) and space-filling molecules (usually glycosaminoglycans' (GAG's)). ECMs are known to attract cells and to promote cellular proliferation by serving as a reservoir of growth factors and cytokines as well as providing the cells with a scaffold.

The ECM material can be obtained from any mammal. It could be derived from, but not limited to, intestinal tissue, bladders, liver, spleen, stomach, lymph nodes or skin. ECM may be derived from human cadaver skin, porcine urinary bladder submucosa (UBS), porcine urinary bladder matrix (UBM), porcine small intestinal submucosa (SIS).

Particles included in the present method can also be, or contain, biological signal molecules e.g. chemo attractants, cytokines and growths factors, polysaccharides, peptides and derivatives of these and the likes. Examples of such materials could be but are not limited to GAG's (chondroitin sulfate, dermatan sulfate, heparan sulfate, hyaluronan, heparin etc.), thrombin, fibrinogen, fibrin, fibronectin, vitronectin, vimentin.

The particles could either consist of one material, cross-linked if necessary, or found in combinations, mixed or cross-linked together.

It is also preferred that the method further comprises the step of cross-linking the non-woven natural protein structure. Various methods of cross-linking exist like glutaraldehyde or 1-Ethyl-3-[3-dimethylaminopropyl]carbodiimide Hydrochloride (EDC), but in this context it is particularly preferred that the cross-linking is done by heat treatment or ultraviolet irradiation or both. Ultraviolet irradiation can be done as a post treatment or as an in-line continuous treatment. Hereby is avoided to use chemicals that are not compatible with introduction into the body as tissue replacements or with introduction onto the body as dressings.

When using the method for producing gelatin non-woven, the best effect of heat treatment is obtained when the produced gelatin fibers are not dried too rapidly such that sufficient time for gelation, which is an orientation taking place on the molecular level, is ensured. This mean, in essence, that the flow and processing temperatures are adjusted to allow for sufficient slow drying to allow gelation. Non-wovens of gelatin produced and treated this way can be beta sterilized with 25 kGy and still be sufficiently cross-linked. This also applies to other structures made of gelatin for instance by freeze-drying. If the drying of fibers is too rapid cross-linking by subsequent heat treatment will still occur but to a lesser degree. Similarly, cross-linking by heat treatment of freeze dried structures will occur to a lesser degree, if the gelatin solution is not allowed to gel before freezing. One aspect of the invention relates to a process of cross-linking a natural protein structure comprising the step allowing the natural protein to gel prior to drying follow by the step freeze-drying.

In one embodiment cross-linking is obtained by heat-treatment. The heat-treatment is even better if a polycarboxylic acid is added to the spinning solution. Such heat treatment could be at 150° C. for 3 h. In one embodiment, it is heat-treated in vacuum. The benefit is that cross-linking is not taking place in the solution, as will be the case with for example glutaraldehyde. Thus a fiber, a non-woven or for instance a freeze-dried structure can be processed with the cross-linking additive present without activating it. Activation for cross-linking can be done as a simple post treatment neither involving hazardous wet chemistry nor needs for energy consumption due to drying of the product nor induction of deformations of the already obtained structure by for example swelling. Examples of usable polycarboxylic acid are poly acrylic acids, citric acid, and carboxy-methyl-cellulose (CMC) but not excluding others.

In one embodiment the cross-linked fiber non-woven is a non-woven that if submerged in 20° C. tap water for 2 minutes, it can be pulled up in 1 piece.

Suitable crosslinkers are polycarboxylic acids, either the free acid or salts thereof. These could be (but are not limited to): Synthetic: poly(acrylic acid), poly(methacrylic acid), poly(methyl-vinyl ether-co-maleic anhydride) (various grades of Gantrez AN), copolymers of acrylic acid and vinylic monomers (vinylpyrrolidone, alkyl vinyl ethers alkylacrylates, alkylmethacrylates, styrene, maleic anhydride, maleic acid, fumaric acid, hydroxyalkylacrylates, hydroxyalkylmethacrylates), copolymers of methacrylic acid and vinylic monomers (vinylpyrrolidone, alkyl vinyl ethers, alkylacrylates, alkylmethacrylates, styrene, maleic anhydride, maleic acid, fumaric acid, hydroxyalkylacrylates, hydroxyalkylmethacrylates) and copolymers and blends of the above; Natural (acidic polysaccharides most preferred): Pectin, carboxymethylcellulose, sodium alginate, gum arabic, Hyaluronic acid, dermatan sulfate, heparin sulfate, heparan sulfate, chondroitin sulfate and blends of the above.

Crosslinking can be chemical crossbinding, where chemical groups react and form covalent bounds. However, the same effect of stabilization will be obtained when complexes are formed resulting in in-solubility. Such complex formation is also considered crosslinking herein.

The thrombin used in preferred embodiments of this aspect of the invention can be of animal or human origin. For example, thrombin obtained from one mammalian species (e.g., bovine, pig, sheep) can be incorporated into compositions of the invention used to treat another mammalian species, for example, humans. More preferably, the thrombin used in the composition is from the same species for which the composition is intended to be used. The term "thrombin" as used herein includes natural thrombin molecules derived from animal or human plasma, and synthetic forms such as those produced by recombinant DNA technology including functionally active analogs that effectively maintain clotting activity in an animal or human. Thrombin is present in the hemostatic composition of the invention in a concentration of 1 to 100 U/cm², and preferably between 10 to 50 U/cm². A unit of thrombin, as used herein, is defined as the amount of thrombin required to clot a standardized 15 l ml fibrinogen (≈250 mg/ml) solution in 15 seconds.

In other preferred embodiments of this aspect of the invention, the hemostatic composition includes fibrinogen. The fibrinogen can be of animal or human origin, and is preferably from the same species for which the composition is intended to be used. By the term "fibrinogen," as used herein, is meant to include natural fibrinogen molecules derived from animal or human plasma, and synthetic forms such as those produced by recombinant DNA technology including functionally active analogs that effectively maintain clotting activity in an animal or human. The fibrinogen used in the compositions of the invention can be highly purified, can contain small amounts of clotting Factor XIII, or can be enriched with clotting Factor XIII. Also preferred is enrichment with Factor VII. Typically, the amount of clottable fibrinogen is present in the hemostatic composition of the invention in a concentration between about 0.05 and 20 mg/cm², preferably between about 1 and 20 mg/cm², and more preferably between about 5 and 15 mg/cm².

What happens is that the natural protein structure comes out through a somewhat wide nozzle. The width of the nozzles also allows the particle to come through without clogging the nozzle. The thinness of the fibers is obtained through the combination of the air-flow emitted and the consequent stretching the fiber as well as the spinning process forming the non-woven. Thus, the diameter of the fibers is a consequence of the production process: the air-pressure, the ejection speed, the viscosity of the solution. One aspect of the invention relates to a non-woven with an average fiber diameter of 0.5 and 300 µm, such as 10 to 30 µm. In one aspect none of the fibers have a diameter of less than 0.5 µm and/or more than 300 µm. In another aspect none of the fibers have a diameter of less then 10 µm and/or more than 30 µm.

One aspect of the invention relates a multi component non-woven as described wherein at least one of the fiber compositions has a larger diameter than at least one other. As illustrated in Example 10, the smaller diameter, the softer the material. When applied e.g. as a wound dressing, softness is key to avoid pressure marks to the surrounding skin and to avoid pain in the open wound. Additionally, smaller diameter provides for a higher surface area in the wound dressing. This, in turn, provides a higher release of substance and a higher absorption.

In one aspect of the invention particles are suspended in the aqueous solution prior to ejection. As the diameter of the nozzle is wider than the diameter of the formed fibers, the particles can have any diameter, up to the diameter of the nozzle, or the particles can be smaller than the diameter of the fibers. Wet, soft, and pliable particles of even larger diameter than the nozzle may be ejected. Thus, in one aspect of the invention the particles suspended in the aqueous solution have a mean diameter wider than the mean diameter of the fibers.

Figure 1:
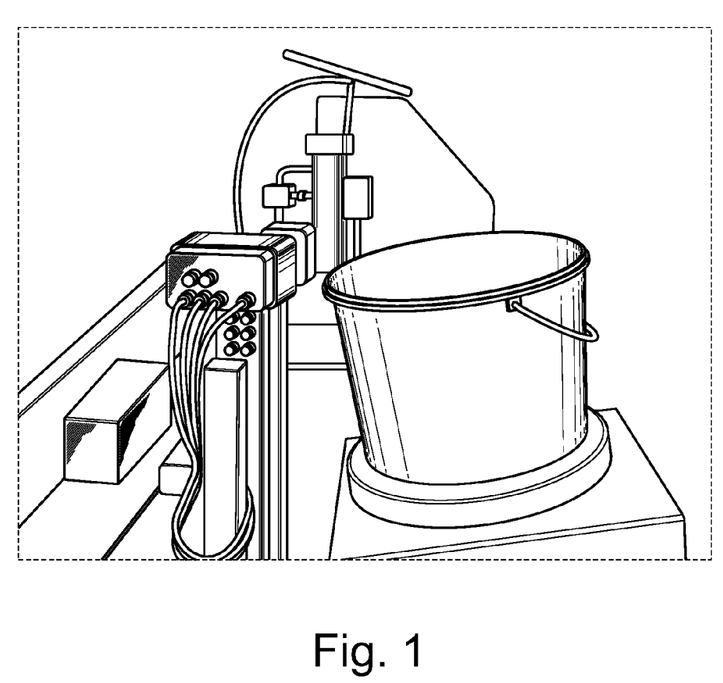
FIG. 1: Labscale production of gelatin non-woven using the inside of a rotating cylinder as the collecting device.
Figure 2:
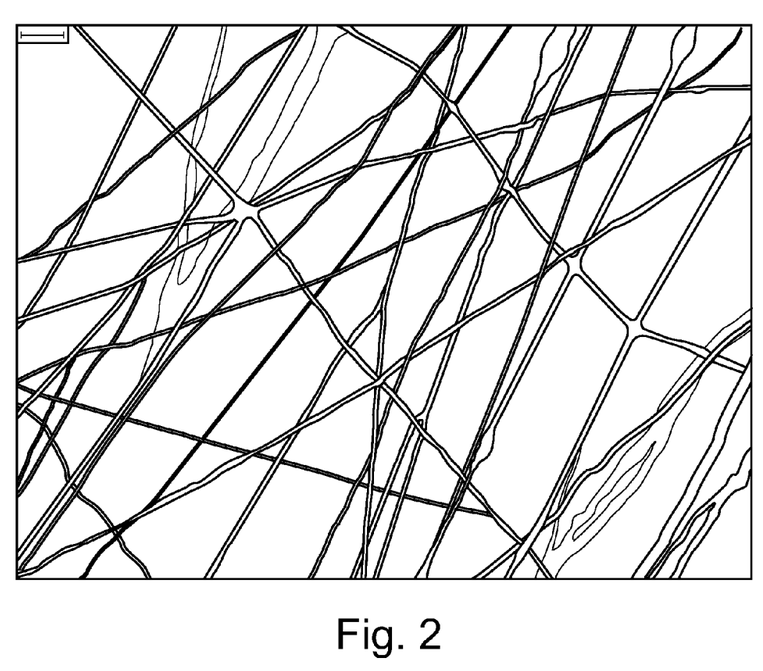
FIG. 2: Gelatin non-woven made from 30% aqueous gelatin. Light microscopy 10× magnification. Scale bar is 50 μm.
Figure 3:
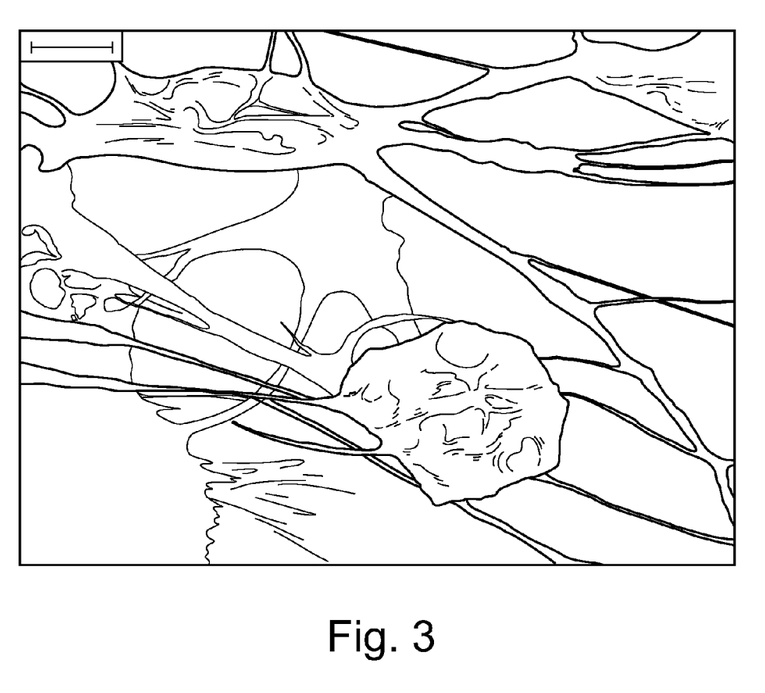
FIG. 3: Gelatin non-woven with UBM particles. Scale bar is 100 μm.
Figure 4:
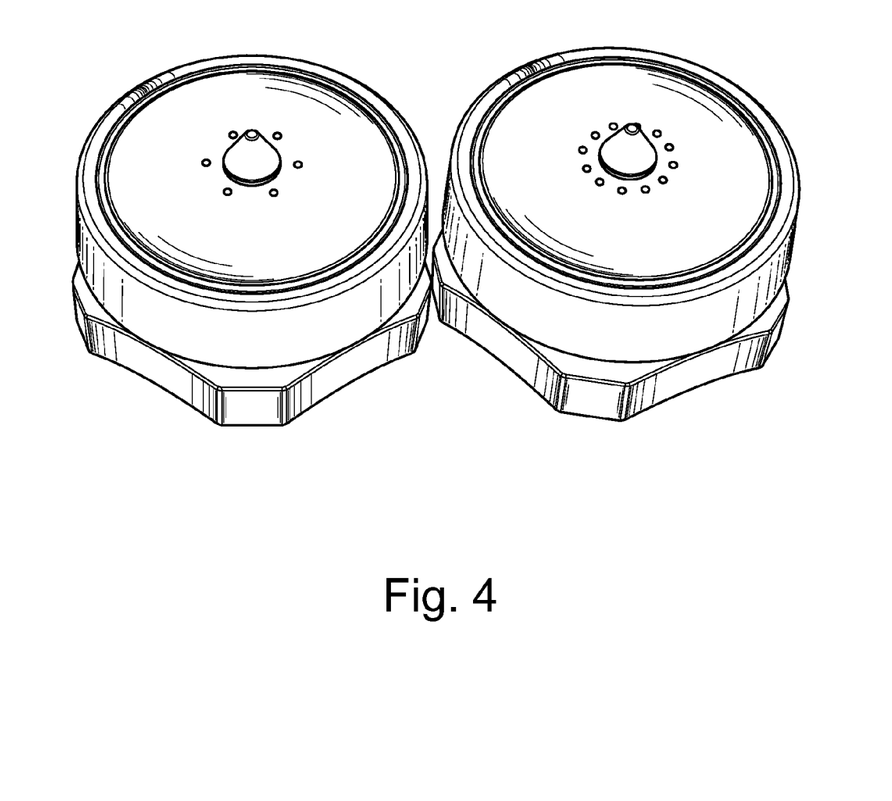
FIG. 4: Picture showing examples of nozzles used to make gelatin non-woven. The orifice is found on the top of the raised center part. There are either 6 or 12 air holes in a circle around the orifice.
Figure 5:
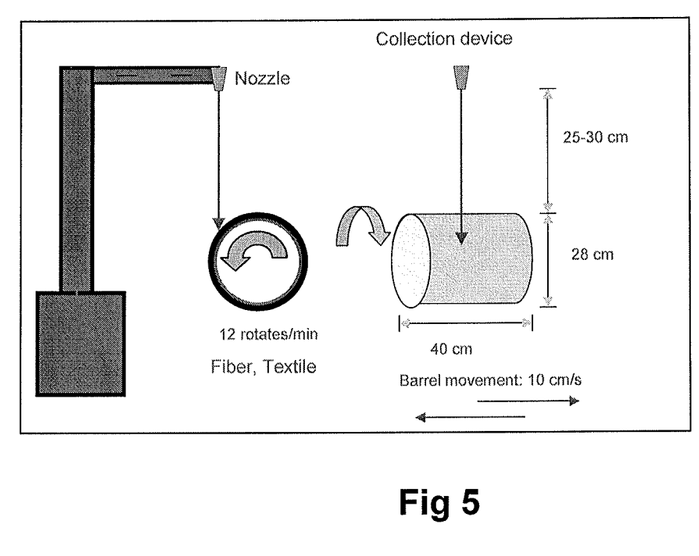
FIG. 5: Is a schematic drawing of a production setup.

As illustrated in FIG. 3, the thin fiber will have bulbs of particles, where the particles are coated with the natural protein structures. It is preferred that the particles are compatible with the natural protein structures, such that coating is strong. That is, the strength of the fiber will be lowered if the particles are not compatible with the natural protein structures. When the term 'particle' is used, it includes materials in the form of flakes, fibers, particles, powder or the like.

EXAMPLES

Example 1

An aqueous solution of type B porcine gelatin with 260 bloom of pharmaceutical grade from Gelita in the ratio of 20 g gelatin to 30 g water and 3 g propanol was prepared. The gelatin was allowed to dissolve in the liquids by heating to 50° C. for several hours. The dissolved gelatin solution was transferred to a can, which fit a small lab-size bulk melter built especially for this purpose. The size of the can used with the bulk melter is approximately from 0.5 liter to 1 liter. The bulk melter heats only the upper surface of the material in the can, which then becomes a viscous liquid and therefore can be pumped to a dispensing unit, mounted hereto. The dispensing unit is a CF-200 Controlled Fiberization Gun provided from Nordson Corp, equipped with a nozzle with 0.012 inch orifice and 6 air holes. The temperature of the bulk melter can be controlled in its different parts. The temperature of the gun can be controlled and the temperature and rate of the air is controlled.

The temperature of the gelatin was kept at approx. 50° C. and the air was not heated. The obtained non-woven was rigid and the resulting fibers had a diameter from 100 to 200 µm.

The air-flow is controlled by a valve. A maximum of approximately 20 l atmospheric air per min is used.

Example 2

In a setup similar to the one described in example 1 a nozzle with an orifice of 0.030 inch (6 air holes) was used. The obtained non-woven was similar in structure to the one described in example 1.

Example 3

In a setup similar to the one described in example 1 the temperature of the gelatin was kept at approximately 92° C., and the air was heated to approximately 92° C. The obtained non-woven was less rigid than in example 1 and fibers were approximately 100 µm wide. A similar result was obtained using a nozzle with an orifice of 0.030 inch.

Example 4

An aqueous solution of porcine gelatin with bloom 300 from Gelita was prepared similar to example 1. The solution contained 30% gelatin and 5% propanol. A nozzle with an orifice of 0.018 inch was used with the equipment mentioned in example 1. A fibrous non-woven structure could be obtained when the collecting device was held in a parallel position to the fiber extruding direction. It was found that an easy way to process a non-woven sheet was when a rotating cylinder was used as a collecting device. In this case the non-woven sheet was collected on the inner vertical surface of the rotating cylinder. While the cylinder was rotating it was furthermore moved in the vertical direction alternating from an upward movement to a downward movement. When a constant rate of the movements of the collecting device was maintained and the rate of fiber output was kept constant it was possible to create a non-woven sheet, which has a uniform appearance.

The powerfulness of this process is seen by the fact that in approximately 5 minutes a non-woven gelatin with an area of app. 1350 cm² and an approximate thickness of app. 2 mm is made.

Example 5

In another experiment similar to example 4a 30% gelatin solution was made in pure water (70%) without alcohol. The fibers of the resulting non-woven had diameters from 3 to 7 µm.

Example 6

In another experiment similar to example 5 a 35% gelatin solution was made. The fibers of the resulting non-woven had diameters from app. 4 to app. 17 µm with an average of app. 9 µm. The non-woven was cross-linked by a heat-treatment. The heat-treatment was done over night in a vacuum oven, which upon evacuation of air was heated to 120° C. The cross-linked fibers swell upon hydration but do not dissolve, which on the other hand was seen with untreated gelatin non-woven.

To evaluate the cell morphology and 3D growth of fibroblasts on gelatin fibers, biopsies were punched out and seeded with primary human fibroblasts (passage 3) on the surface with a density of $2.5 \times 10^4$ cells/cm$^2$ in a small volume of growth medium (10% FCS in DMEM) containing antibiotics (penicillin, streptomycin and Amphotericin B). The scaffolds were incubated at 37° C. at 5% $CO_2$ before additional growth medium was added. Evaluation of the cells attachment, morphology, growth and population of the scaffold were preformed on day 1, 3 and 7 by staining the cells with neutral red followed by evaluation using an Leica DMIRE2 inverted microscope fitted with a Evolution MP cooled colour camera (Media Cybernetics). Digital images were taken using Image Pro Plus 5.1 software (Media Cybernetics).

The fibroblasts were adhering to the fibers as spindle-shaped cells growing on single fibers except in regions where several fibers were crossing each other. These cells were growing across the fibers. There was a continuous increase in cells number from the start of the study at day 1 to day 7.

Example 7

In another experiment with a setup similar to the one described in example 6 a 24% gelatin solution was used. In the gelatin solution particles of porcine urinary bladder matrix (UBM) was mixed in. The dry matter of the UBM particles was 30% of the dry matter of gelatin. The average particle size of the particles was approximately 150 µm. A nozzle with an orifice of 0.030 inch was used. The fibers were cross-linked by a heat-treatment similar to the one described in example 6. The resulting non-woven had fibers with diameter from app. 3 µm to app. 15 µm with an average of app. 7 µm.

In order to evaluate the cell morphology and 3D growth of fibroblasts on gelatin fibers+/−UBM particles, biopsies were punched out of each type of the scaffolds and seeded with primary human fibroblasts (passage 3) on the surface with a density of $2.5 \times 10^4$ cells/cm$^2$ in a small volume of growth medium (10% FCS in DMEM) containing antibiotics (penicillin, streptomycin and Amphotericin B). The scaffolds were incubated at 37° C. at 5% $CO_2$ before additional growth medium was added. Evaluation of the cells attachment, morphology, growth and population of the scaffold were preformed on day 1, 3 and 7 by staining the cells with neutral red followed by evaluation using an Leica DMIRE2 inverted microscope fitted with a Evolution MP cooled colour camera (Media Cybernetics). Digital images were taken using Image Pro Plus 5.1 software (Media Cybernetics).

The cell growth showed on both types of gelatin fibers (+/−UBM particles) and on all days tested adherent cells growing as spindle-shaped cells. The cells were growing around the fibers and in areas where several fibers were crossing each other the cells were stretching across the fibers. At the first days of the study no difference was seen between having UBM particles in the scaffold or not but at day 7 it was apparent that the cells were more dispersed in the scaffold containing UBM particles compared to the pure scaffold and also contracted this scaffolds more. There were a continuously increase in cells number from day 1 and to day 7.

One large SPF pig (crossbred of Durac, Yorkshire and Danish landrace at Lab Scantox, Denmark) had circular full-thickness wounds approximately 20 mm in diameter. The non-woven with UBM (20 mm disc), tested in duplicates, was carefully applied on top of the wound-bed. To obtain optimal contact to the wound-bed, each material was held in place by a 20 mm pre-wetted foam plug and covered by foam dressings. On day 2 the top-foam dressing was removed and the foam plug was very carefully removed, so as not to disturb the healing and to ensure that the sample materials remain in full contact with the wound bed. The wounds were covered by a hydrocolloid dressing (Comfeel Plus) and changed on day 3, 6, 8, 10, 12 and 15. Following euthanasia, each wound was cut free as a block separated from skeletal muscle tissue and fixed in 10% neutral buffered formalin. The fixed samples were paraffin embedded and sectioned in 5 µm slices stained with haematoxylin and eosin (HE) for general structure of tissue, Masson's trichroma for newly formed collagen and von Willebrand factor for angiogenesis. The evaluation was preformed by a trained pathologist at Lab Scantox.

Massive amounts of granulation tissue developed was observed consisting mainly of large numbers of thin-walled blood vessels and fibrocytes/fibroblasts (fibrovascular connective tissue). Moderate amounts of newly formed collagen and slight angiogenesis were present in the wounds. A minimal presence of foreign material likely to be test item was recorded and minimal numbers of clear vacuoles were observed in the profound granulation tissue.

In the superficial parts of the wounds a moderate to marked inflammation was found. In the deeper parts of the wounds a marked inflammation was present. Marked numbers of giant cells were seen and minimal to slight haemorrhage was recorded.

The re-epithelialisation was slight and the thickness of the epithelium was marked in some cases with rete-ridge formation.

In conclusion, no significantly difference in the histopathological wound healings parameters assessed were detected between the non-woven and the untreated control wounds. However a tendency towards more giant cells were seen in the treated wounds compared to control wounds, probably reflecting a foreign reaction to the non-woven, a common and naturally reaction to materials left in wounds.

Example 8

Multi-Nozzle Set Up for Combined Scaffolds

Multi component gelatine scaffold may be produced by combining several lab-size bulk melters in a set up. In each lab-size bulk melter there is a gelatine solution/gel containing different components.

One example is using two containers and two nozzle systems. In one container there is a 30% gelatine solution in water containing 1000 IU thrombin/ml. In the other container there is a 30% gelatine solution in water containing 6 mg fibrinogen/ml. The solutions may also contain an alcohol for regulating the viscosity and fast evaporation of the solvent. When forming the fibres it is important that the fibres are dry when touching each other on the support layer otherwise the polymerisation reaction of fibrinogen may initiate.

If the scaffold/non woven should be used as a haemostasis sheet depending on the situation the scaffolds may be cross-linked as described in example 6 but using lower temperature but longer time or if a fast reaction is needed it may remain un-cross-linked.

Example 8

Another example is the possibility to combine fibres with different diameters by using nozzles with different orifice. The scaffold/non-woven is cross-linked and used as scaffold for tissue regeneration.

Example 9

Figure 6:
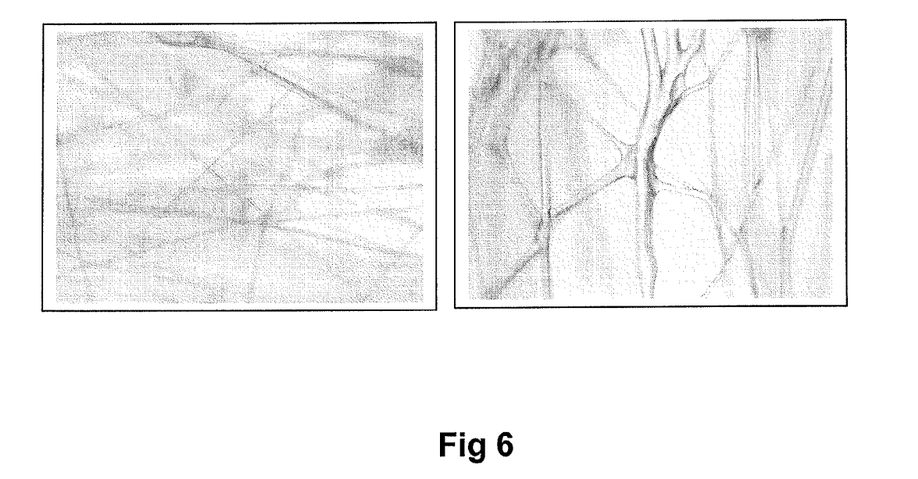
FIG. 6: The collected non-woven sheets from example 10 (left) and example 9 (right).
Figure 7:
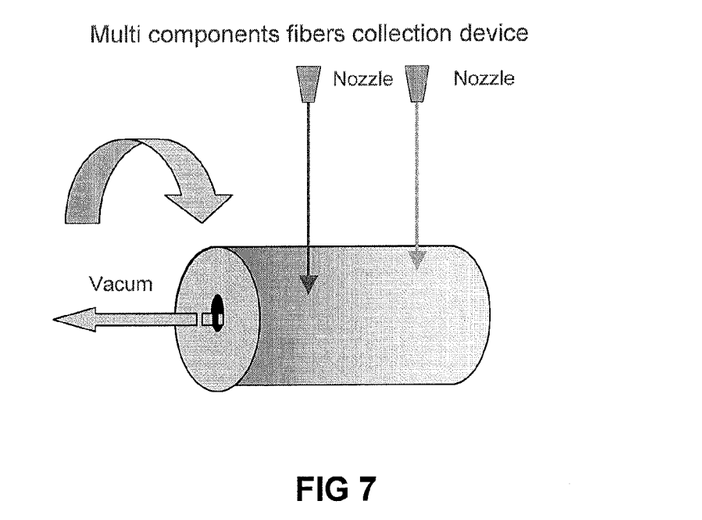
FIG. 7: Is a detailed drawing of a production setup.
Figure 8:
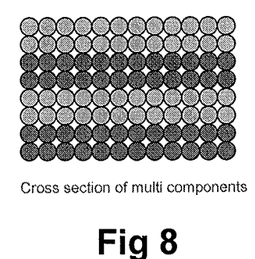
FIG. 8: Cross section of multi components.

An aqueous solution of porcine gelatine with bloom 300 from Gelita was prepared similar to example 1. The concentration of gelatine is 22%. A nozzle with an orifice of 0.012 inch was used in the equipment. A fibrous non-woven structure could be obtained when the collecting device was held in a vertical position to the fiber extruding direction (see the drawing). In this case the non-woven sheet was collected on a piece of textile which was wrapped on the outside surface of a rotating plastic barrel. The rotation direction of the barrel was same as the fiber's extruding direction. While the barrel collected the fibers, it was rotating and moving from side to side. The advantages of this collecting process is that the collected non-woven fiber sheet is homogeneous.

Example 10

In another experiment with a set up similar to the one described in example 9, the pump speed, which was used to pump 22% gelatine solution in water to the dispensing unit, run at half speed compared to the pump speed at example 1. A nozzle with an orifice of 0.012 inch was applied in this experiment. The diameter of the obtained fibers at a low pumping speed was approximately 5 µm. The softness of the non-woven sheet increased due to the fiber diameter was decreased.

The conclusion was that the diameter of fibers decreased with decreasing the speed of pumping gelatine solution to the dispensing unit. The diameter of fibers at a low gelatine pumping speed was uniform. The softness of non-woven sheet increased with decreasing the diameter of the fibers.

Example 11

In another experiment with a system with dual set up similar to the one described in example 1 were established for dispensing gelatine fibers and gelatine fibers with thrombin.

One of the set ups had a 22% gelatine solution in water, and the other was a 22% gelatine solution in water containing 1000 IU/ml thrombin. The gelatine solution and the thrombin solution were pumped to the dispensing units individually. Each of dispensing unit had a nozzle with an orifice of 0.012 inch. The distance between two was 10 cm. The experiment was carried out in a clean room with a low humidity.

A non-woven sheet collector similar to the one in example 9 was used to collect the dispensed fibers.

A home use vacuum cleaner was connected to the sidewall of the barrel to suck the ambient dry air through the multi holes (I.D. 5 mm) on the surface of the barrel into the inside of the barrel. The ambient air dried the dispensed fibers rapidly on the textile to prevent a cross contamination between the gelatine fibers and the thrombin fibers.

The benefit of implementation of a vacuum system in the collection device is to speed up the process of drying the dispensed fibers for preventing a cross contamination between the multi components fibers, and cut down the risk of spreading the thrombin in the ambient air during the production processes.

The invention claimed is:

1. A method for preparation of a non-woven comprising the steps of:
    (a) ejecting an aqueous alcoholic solution of gelatin comprising thrombin through a nozzle to form gelatin fibers containing thrombin, wherein the aqueous alcoholic solution comprises less than 25% by volume of a low molecular weight alcohol;
    (b) ejecting an aqueous alcoholic solution of gelatin comprising fibrinogen through a nozzle to form gelatin fibers containing fibrinogen, wherein the aqueous alcoholic solution comprises less than 25% by volume of a low molecular weight alcohol; while
    (c) emitting pressurized air into the gelatin fibers containing thrombin and the gelatin fibers containing fibrinogen exiting the nozzles to attenuate or stretch the gelatin fibers containing the thrombin and the gelatin fibers containing the fibrinogen; and
    (d) collecting the gelatin fibers containing the thrombin and the gelatin fibers containing the fibrinogen on a collecting device to form a non-woven multiple-component gelatin scaffold comprising thrombin and fibrinogen.

2. The method of claim 1, wherein the pressurized air is emitted from air jet bores.

3. The method according to claim 1, wherein the gelatin fiber is biodegradable.

* * * * *